United States Patent [19]
Giometti

[11] Patent Number: 5,351,552
[45] Date of Patent: Oct. 4, 1994

[54] MACHINE FOR SQUEEZE TESTING GLASS CONTAINERS

[75] Inventor: Stephen M. Giometti, Horseheads, N.Y.

[73] Assignee: Emhart Glass Machinery Investments Inc., Wilmington, Del.

[21] Appl. No.: 151,189

[22] Filed: Nov. 10, 1993

[51] Int. Cl.$^5$ .............................................. G01N 3/08
[52] U.S. Cl. ...................................... 73/824; 73/818; 209/599
[58] Field of Search ................ 73/818, 819, 820, 821, 73/822, 823, 824; 209/599

[56] References Cited

U.S. PATENT DOCUMENTS

| | | | |
|---|---|---|---|
| 3,702,563 | 11/1972 | Brady et al. | 73/824 |
| 3,729,082 | 4/1973 | Federko | 198/459 |
| 3,765,231 | 10/1973 | Erb et al. | 73/824 |
| 3,777,556 | 12/1973 | Zappia | 73/825 |
| 4,021,122 | 5/1977 | Krenmayr | 356/240 |
| 4,077,254 | 4/1978 | Mercer, Jr. et al. | 73/824 |
| 4,096,939 | 6/1978 | Riggs et al. | 198/460 |
| 4,479,582 | 10/1984 | Ducloux | 209/552 |

FOREIGN PATENT DOCUMENTS

| | | | |
|---|---|---|---|
| 0126228 | 7/1984 | Japan | 73/818 |
| 0135343 | 8/1984 | Japan | 73/818 |

Primary Examiner—Hezron E. Williams
Assistant Examiner—James M. Olsen
Attorney, Agent, or Firm—Spencer T. Smith

[57] ABSTRACT

A machine for squeeze testing glass containers comprising a test station, including a fixed pad having a curved container engaging surface and an opposed wheel selectively spaced from the surface, rotating at a predetermined surface speed and in the direction required to roll a container delivered to the station along the curved surface until it is released therefrom. A conveyor delivers containers to the test station and carrys released containers away from the test station. A roller is rotatable about an axis parallel to the axis of rotation of the wheel and defines with the wheel a path through which released containers will pass. The roller is biased forward to a selected location whereat the distance between the roller and the wheel is less than the outer diameter of a released container, and the roller is rotated at a surface speed selected to reduce the rotation of a released container, which passes between the wheel and the roller.

3 Claims, 2 Drawing Sheets

MACHINE FOR SQUEEZE TESTING GLASS CONTAINERS

Squeeze testing, also known as simulated impact testing is a common test performed on glass bottles during the manufacturing process. Squeeze testing involves placing a bottle under stress to cause weak bottles to break. The stress is caused by placing a load on one side of the bottle as the bottle rolls along a shoe or pad. This method places a uniform stress all the way around the bottle during the test. Glass is a brittle material and like most brittle materials, it is strong in compression and weak in tension. By loading the bottle in the described manner, the bottle walls receive an alternating stress. This stress causes a bottle to fail or break if the bottle has any structural flaws in its sidewall. "Good" bottles withstand the stress and are undamaged.

Bottles to be tested are delivered by a conveyor to the entrance of a squeeze testing path defined between a portion of the outer diameter of a rotating wheel and a stationary shoe or pad which has a curved surface approximating the radius of the wheel. The wheel (or the pad) is biased against the bottle using an air device such as an air cylinder or an air spring and the wheel rotates to forcefully roll the compressed bottle along the pad curved surface. The load applied is varied by adjusting the air supply pressure or the spring force and the wheel (or pad) mounting permits movement of the wheel in the direction of the load so that it can track irregularities in the bottle's surface. When such prior art machines operate at rates in excess of 250 bottles per minute handling difficulties appear which are undesirable. U.S. Pat. No. 3,831,437 discloses an earlier squeeze tester.

It is an object of the present invention to provide an improved squeeze testing machine which can handle bottles at a rate of 350 bottles per minute or higher.

Other objects and advantages of the present invention will become apparent from the following portion of this specification and from the accompanying drawings which illustrate in accordance with the mandate of the patent statutes a presently preferred embodiment incorporating the principles of the invention.

Figure 1:
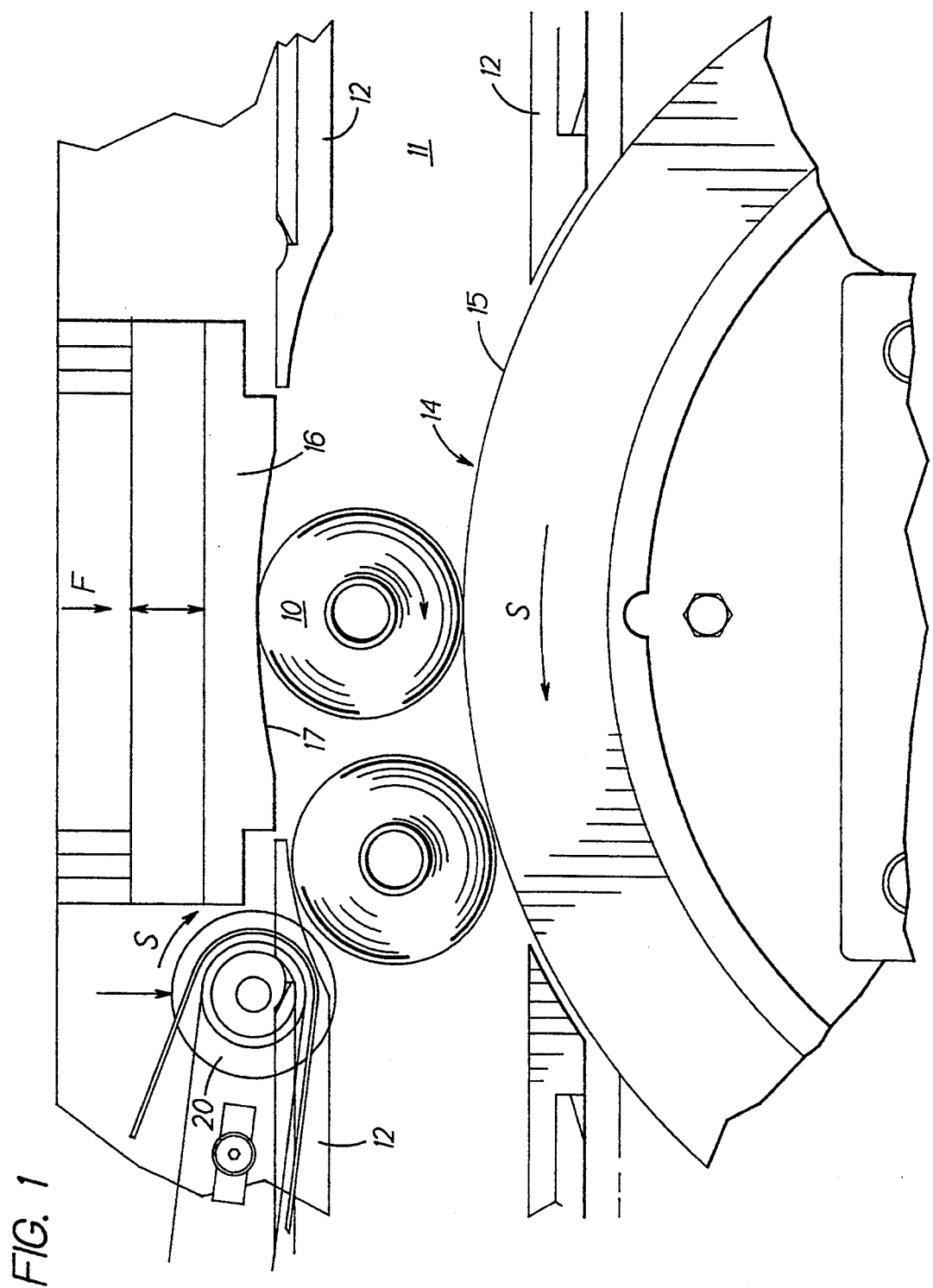
FIG. 1 is a top view of a portion of the squeeze testing machine made in accordance with the teachings of the present invention.

Bottles 10 are carried by a conveyor 11 and contained within opposed guide rails 12 which guide the bottles into engagement with a squeeze wheel 14 which is rotating at a constant surface speed S in the counterclockwise direction. The engaged bottle enters a pathway defined between a portion of the wheel surface 15 and a shoe or pad 16 which has a curved surface 17 approximately the same radius as the surface 15 of the wheel 14.

The pad, while having a fixed position, is resiliently biased against the bottle to compress the bottle by a force F that can be varied as desired. The bottle rolls in compression along this curved path of the shoe or pad and has a surface speed (rotating clockwise) equal to the surface speed of the wheel.

When the tested bottle leaves the pad it is guided by the upper exit guide 12 towards a pair of vertically stacked cylindrical rollers 20 which are rotatively driven about a vertical axis at the same surface speed S as the surface speed of the squeeze wheel 14 and which are biased toward the squeeze wheel to define a path slightly smaller than the bottle. The bottle is engaged simultaneously by the squeeze wheel 14 and the rollers 20 which are rotating at the same surface speed with the rollers rotating clockwise and the squeeze wheel rotating counterclockwise. A bottle leaves this passageway having no rotation or a slow enough rotation or spin so that the bottle remains stable and can be carried by the conveyor away from the test location.

Figure 2:
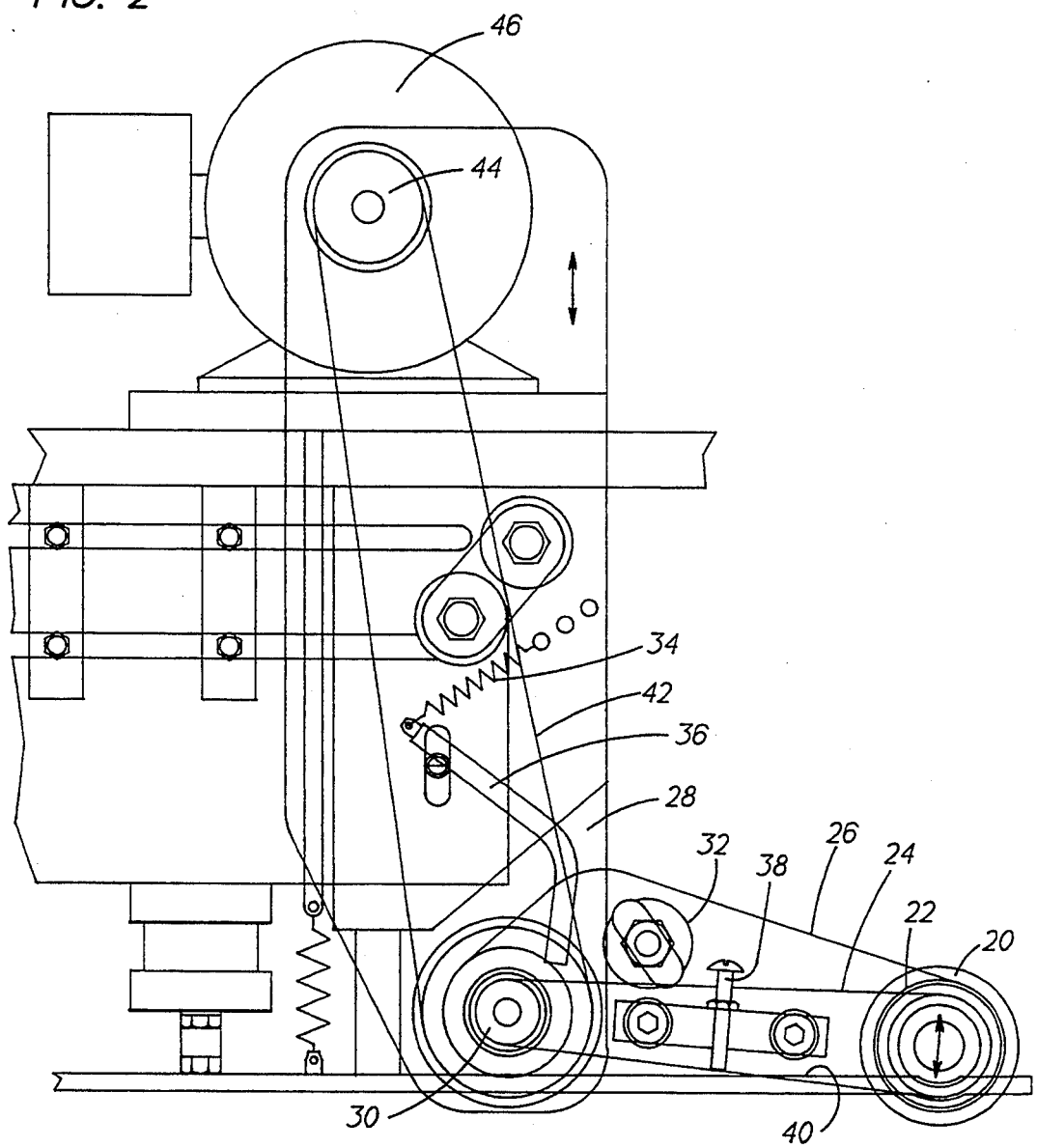
FIG. 2 is a top view of another portion of the machine.

Referring to FIG. 2, the roller pair 20 is supported on a pulley 22 which is driven by a belt 24. The pulley 22 is supported on a bracket 26 which is pivotally secured to the assembly frame 28 and a second pulley 30 is also supported on this bracket. The belt path is defined by these pulleys and by an idler roller 32. The bracket is urged in the clockwise direction by a spring 34 which pulls on a lever 36 secured to the bracket. Clockwise movement is limited by an adjustable stop screw 38 which engages a frame rail 40. The second pulley is driven by a second belt 42 which is driven off the hub 44 of a motor 46.

The entire assembly and the assembly supporting the shoe or pad 16 are displaceable towards and away from the conveyor so that different sized bottles can be tested. Additionally, if desired, the shoe or pad can be designed to have a curvature and length matched to the diameter of the bottle being tested and can be replaced with another shoe or pad when a different sized bottle is to be tested.

I claim:

1. A machine for squeeze testing glass containers comprising
    a test station including
        a fixed pad having a curved container engaging surface and
        an opposed wheel selectively spaced from said surface and rotating at a predetermined surface speed and in the direction required to roll a container delivered to the station along said curved surface until it is released therefrom,
    a conveyor for delivering containers to said test station and for carrying released containers away from said test station,
    roller means rotatable about an axis parallel to the axis of rotation of said wheel and located to define with said wheel a path through which released containers will pass,
    means for resiliently urging said roller means to a selected location whereat the distance between said roller means and said wheel is less than the outer diameter of a released container, and
    means for rotating said roller means at a surface speed selected to reduce the rotation of a released container.

2. A machine for squeeze testing glass containers according to claim 1, wherein the surface speed of said rotating roller means is substantially the same as the surface speed of said wheel.

3. A machine for squeeze testing glass containers according to claim 1, further comprising a guide for guiding released containers to said path between said roller means and said wheel.

* * * * *